United States Patent [19]

Eistetter et al.

[11] 4,337,267
[45] Jun. 29, 1982

[54] PHENALKOXYALKYL- AND PHENOXYALKYL-SUBSTITUTED OXIRANECARBOXYLIC ACIDS, THEIR USE AND MEDICAMENTS CONTAINING THEM

[75] Inventors: Klaus Eistetter, Constance; Erich Rapp, Radolfzell, both of Fed. Rep. of Germany

[73] Assignee: Byk Gulden Lomberg Chemische Fabrik GmbH, Constance, Fed. Rep. of Germany

[21] Appl. No.: 250,627

[22] Filed: Apr. 3, 1981

Related U.S. Application Data

[63] Continuation-in-part of Ser. No. 182,935, Sep. 2, 1980, abandoned.

[30] Foreign Application Priority Data

Aug. 25, 1980 [CH] Switzerland ............................ 6397/80
Mar. 6, 1981 [CH] Switzerland ............................ 1526/81

[51] Int. Cl.$^3$ .................... A61K 31/335; C07D 303/48
[52] U.S. Cl. ...................................... 424/278; 549/549
[58] Field of Search ...................... 260/348.58, 348.49; 424/278

[56] References Cited

U.S. PATENT DOCUMENTS 4,132,719 1/1979 Mohrbacher .................. 260/348.48
4,132,720 1/1979 Mohrbacher .................. 260/348.61
4,196,300 4/1980 Mohrbacher .......................... 549/90

OTHER PUBLICATIONS

OESCH, "Hepatic Epoxide Hydrase, Structure-Activity Relationships for Substrates and Inhibitors", (Biochemistry, vol. 10, No. 26, 4858 to 4866, 1971).

Primary Examiner—Norma S. Milestone
Attorney, Agent, or Firm—Berman, Aisenberg & Platt

[57] ABSTRACT

Phenalkoxyalky- and phenoxyalkyl-substituted oxiranecarboxylic acids of the formula

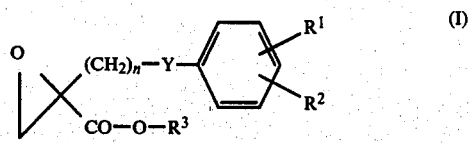

wherein
  $R^1$ denotes a hydrogen atom (—H), a halogen atom, a lower alkyl group, a lower alkoxy group, a nitro group or a trifluoromethyl group,
  $R^2$ has one of the meanings of $R^1$,
  $R^3$ denotes a hydrogen atom (—H) or a lower alkyl group,
  Y denotes —O—$(CH_2)_m$—,
  m denotes 0 or an integer from 1 to 4, and
  n denotes an integer from 2 to 8, with the proviso that the sum of m and n is an integer from 2 to 8, and the salts of the acids are new compounds. They display a hypoglycaemic action in warm-blooded animals. Processes for the preparation of the new compounds and of the intermediate products required for their preparation are described.

13 Claims, No Drawings

PHENALKOXYALKYL- AND PHENOXYALKYL-SUBSTITUTED OXIRANECARBOXYLIC ACIDS, THEIR USE AND MEDICAMENTS CONTAINING THEM

RELATED APPLICATION

This application is a continuation-in-part of application Ser. No. 182,935 filed Sept. 2, 1980 now abandoned.

TECHNICAL FIELD

The invention relates to phenalkoxyalkyl- and phenoxyalkyl-substituted oxiranecarboxylic acids, processes for their preparation, their use and medicaments containing them.

BACKGROUND

Phenoxymethyloxiranes, for example 2-(4-nitrophenoxymethyl)-oxirane, and phenyloxiranecarboxylic acid esters, for example 2-phenyloxirane-2-carboxylic acid ethyl ester, inter alia, are within the scope of an investigation into the ability of substituted cyclic compounds (with a three-membered ring) to serve as a substrate or inhibitor for epoxide hydrase from guinea pig liver microsomes [F. Oesch et al., Biochem., 10 (1971) No. 26, 4,858–66]. Phenalkoxyalkyl- and phenoxyalkyl-substituted oxiranecarboxylic acids have now been found to be pharmaceutically-active compounds with a specific action.

SUMMARY OF THE INVENTION

Pharmaceutically-active phenalkoxyalkyl- and phenoxyalkyl-substituted oxiranecarboxylic acids, their pharmacologically-acceptable salts and their lower alkyl esters have a hypoglycemic and hypoketonemic activity which makes them useful for the prophylaxis and treatment of disorders, such as diabetes, based on glucose or fat metabolism. The compounds are administered enterally or parenterally in conventional dosage forms to those subject to or afflicted with such disorders. The dosage forms ordinarily comprise compositions in which the active ingredient is in admixture with a suitable excipient or carrier.

The following types of acids are illustrative of the compound aspect of this invention; corresponding salts and lower alkyl esters are readily appreciated by any man skilled in the art:

2-[ω-phenoxy($C_{2-8}$)alkylene]oxirane-2-carboxylic acid,
2-[ω-(monosubstituted)phenoxy($C_{2-8}$)alkylene]oxirane-2-carboxylic acid,
2-[ω-(disubstituted)phenoxy($C_{2-8}$)alkylene]oxirane-2-carboxylic acid,
2-[ω-benzyloxy($C_{2-7}$)alkylene]oxirane-2-carboxylic acid,
2-[ω-(monosubstituted)benzyloxy($C_{2-7}$)alkylene]oxirane-2-carboxylic acid,
2-[ω-(disubstituted)benzyloxy($C_{2-7}$)alkylene]oxirane-2-carboxylic acid,
2-[ω-(2-phenylethoxy) ($C_{2-6}$)alkylene]oxirane-2-carboxylic acid,
2-{ω-[2-(monosubstituted)phenylethoxy($C_{2-6}$)alkylene}oxirane-2-carboxylic acid,
2-{ω-[2-(disubstituted)phenylethoxy]($C_{2-6}$)alkylene}oxirane-2-carboxylic acid,
2[ω-(3-phenylpropoxy) ($C_{2-5}$)alkylene]oxirane-2-carboxylic acid,
2-{ω-[3-(monosubstituted)phenylpropoxy]($C_{2-5}$)alkylene}oxirane-2-carboxylic acid,
2-{ω-[3-(disubstituted)phenylpropoxy]($C_{2-5}$)alkylene}oxirane-2-carboxylic acid,
2-[ω-(4-phenylbutoxy) ($C_{2-4}$)alkylene]oxirane-2-carboxylic acid,
2-{ω-[4-(monosubstituted)phenylbutoxy]($C_{2-4}$)alkylene}oxirane-2-carboxylic acid, and
2-{ω-[4-(disubstituted)phenylbutoxy]($C_{2-4}$)alkylene}oxirane-2-carboxylic acid.

Details

More particularly, the invention relates to substituted oxiranecarboxylic acids of the formula

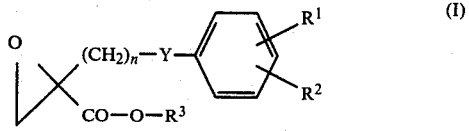

wherein
R[1] denotes a hydrogen atom (—H), a halogen atom, a lower alkyl group, a lower alkoxy group, a nitro group or a trifluoromethyl group,
R[2] has one of the meanings of R[1],
R[3] denotes a hydrogen atom (—H) or a lower alkyl group,
Y denotes —O—$(CH_2)_m$—,
m denotes 0 or an integer from 1 to 4 and
n denotes an integer from 2 to 8, with the proviso that the sum of m and n is an integer from 2 to 8, and salts of the carboxylic acids.

The lower alkyl groups include straight-chain and branched alkyl radicals with from 1 to 4 carbon atoms. Examples of straight-chain alkyl radicals are the methyl, ethyl, n-propyl and n-butyl radical, of which those with 1 or 2 carbon atoms are preferred. Examples of branched alkyl radicals are the isopropyl, isobutyl and sec.-butyl radical, of which that with 3 carbon atoms is preferred. Alkyl radicals in lower alkoxy groups are similarly both straight-chain and branched lower alkyl groups. The methoxy group is the preferred lower alkoxy group.

Halogen atoms are fluorine, chlorine and bromine atoms, of which fluorine and, in particular, chlorine are preferred.

Substituents R[1] and R[2] are preferably in the meta-position or para-position of the phenyl ring.

Salts include those with either an inorganic or an organic base. Pharmacologically-unacceptable salts are readily converted into pharmacologically-, that is to say biologically-, acceptable salts (which are preferred salts according to the invention) by conventional methods. Cations used for salt formation are, advantageously, those of alkali metals, alkaline-earth metals or earth metals, but cations corresponding to organic nitrogen bases, such as amines, aminoalkanols, aminosugars and basic aminoacids, are optionally used.

Exemplary salts are those of lithium, sodium, potassium, magnesium, calcium, aluminum, ethylenediamine, dimethylamine, diethylamine, morpholine, piperidine, piperazine, N-(lower alkyl)-piperazine (for example N-methylpiperazine), methylcyclohexylamine, benzylamine, ethanolamine, diethanolamine, triethanolamine, tris-(hydroxymethyl)aminomethane, 2-amino-2-methylpropanol, 2-amino-2-methyl-1,3-propanediol, glucamine, N-methylglucamine, glucosamine, N-methylglucosamine, lysine, ornithine, arginine and quinoline.

Phenalkoxyalkyl- and phenoxyalkyl-substituted oxiranecarboxylic acids I* of formula I, wherein $R^1$ and $R^2$ are in the meta-position or para-position and $R^1$ denotes a hydrogen atom (—H), a chlorine atom, a methyl group, a methoxy group, a nitro group or a trifluoromethyl group, $R^2$ denotes a hydrogen atom (—H) or a chlorine atom, $R^3$ denotes a hydrogen atom (—H) or a lower alkyl group, Y denotes —O—$(CH_2)_m$—, m denotes 0 or 1 and n denotes an integer from 3 to 7, with the proviso that the sum of m and n is an integer from 3 to 7, and salts of the carboxylic acids form an embodiment of the invention.

Phenoxyalkyl-substituted oxiranecarboxylic acids I** of formula I,
wherein
$R^1$ and $R^2$ are in the meta-position or para-position and $R^1$ denotes a hydrogen atom (—H), a chlorine atom or a trifluoromethyl group, $R^2$ denotes a hydrogen atom (—H), $R^3$ denotes a hydrogen atom (—H), a methyl group or an ethyl group, Y denotes —O— and n denotes 4 to 6, and pharmacologically-acceptable salts of the carboxylic acids with an inorganic or organic base form a preferred embodiment of the invention.

Examples of compounds according to the invention are:

2-[2-(4-chlorobenzyloxy)ethyl]oxirane-2-carboxylic acid ethyl ester,

2-[3-(3-chlorobenzyloxy)propyl]oxirane-2-carboxylic acid methyl ester,

2-[4-(4-fluorobenzyloxy)butyl]oxirane-2-carboxylic acid isopropyl ester,

2-[2-(4-bromophenoxy)ethyl]oxirane-2-carboxylic acid propyl ester,

2-[2-(4-methoxyphenoxy)ethyl]oxirane-2-carboxylic acid ethyl ester,

2-[2-(4-nitrophenoxy)ethyl]oxirane-2-carboxylic acid methyl ester,

2-[2-(4-chlorophenoxy)ethyl]oxirane-2-carboxylic acid n-butyl ester,

2-[2-(4-methoxyphenoxy)ethyl]oxirane-2-carboxylic acid methyl ester,

2-[2-(3-trifluoromethylphenoxy)ethyl]oxirane-2-carboxylic acid ethyl ester,

2-[3-(3-fluorophenoxy)propyl]oxirane-2-carboxylic acid ethyl ester,

2-[3-(4-bromophenoxy)propyl]oxirane-2-carboxylic acid methyl ester,

2-[3-(3-methylphenoxy)propyl]oxirane-2-carboxylic acid sec.-butyl ester,

2-[3-{4-(n-butoxy)phenoxy}propyl]oxirane-2-carboxylic acid ethyl ester,

2-[3-(2-isopropylphenoxy)propyl]oxirane-2-carboxylic acid isopropyl ester,

2-[3-(4-chlorophenoxy)propyl]oxirane-2-carboxylic acid methyl ester,

2-[3-(3-trifluoromethylphenoxy)propyl]oxirane-2-carboxylic acid n-butyl ester,

2-[4-(4-bromophenoxy)butyl]oxirane-2-carboxylic acid ethyl ester,

2-[4-(4-chlorophenoxy)butyl]oxirane-2-carboxylic acid n-propyl ester,

2-[4-(3,4-dichlorophenoxy)butyl]oxirane-2-carboxylic acid ethyl ester,

2-[4-(3-chloro-4-methylphenoxy)butyl]oxirane-2-carboxylic acid methyl ester,

2-[4-(3-methylphenoxy)butyl]oxirane-2-carboxylic acid ethyl ester,

2-[5-(2,5-dimethoxyphenoxy)pentyl]oxirane-2-carboxylic acid ethyl ester,

2-[5-(3-trifluoromethylphenoxy)pentyl]oxirane-2-carboxylic acid n-butyl ester,

2-[5-(4-methylphenoxy)pentyl]oxirane-2-carboxylic acid methyl ester,

2-[5-(3-chlorophenoxy)pentyl]oxirane-2-carboxylic acid isobutyl ester,

2-[5-(4-nitrophenoxy)pentyl]oxirane-2-carboxylic acid ethyl ester,

2-[6-(4-fluorophenoxy)hexyl]oxirane-2-carboxylic acid ethyl ester,

2-[6-(4-trifluoromethylphenoxy)hexyl]oxirane-2-carboxylic acid methyl ester,

2-[6-(3,4-dichlorophenoxy)hexyl]oxirane-2-carboxylic acid n-butyl ester,

2-[6-(4-chlorophenoxy)hexyl]oxirane-2-carboxylic acid isopropyl ester,

2-[7-(3-fluorophenoxy)heptyl]oxirane-2-carboxylic acid ethyl ester,

2-[7-(4-trifluoromethylphenoxy)heptyl]oxirane-2-carboxylic acid ethyl ester,

2[7-(3-chloro-4-methylphenoxy)heptyl]oxirane-2-carboxylic acid methyl ester,

2[7-(3-chlorophenoxy)heptyl]oxirane-2-carboxylic acid n-propyl ester,

2-[8-(4-fluorophenoxy)octyl]oxirane-2-carboxylic acid ethyl ester,

2-[8-(3-trifluoromethylphenoxy)octyl]oxirane-2-carboxylic methyl ester,

2-[8-(3,4-dichlorophenoxy)octyl]oxirane-2-carboxylic acid ethyl ester,

2-[8-(4-chlorophenoxy)octyl]oxirane-2-carboxylic acid isobutyl ester,

2-[2-(2-phenylethoxy)ethyl]oxirane-2-carboxylic acid ethyl ester,

2-{2-[2-(4-chlorophenyl)ethoxy]ethyl}oxirane-2-carboxylic acid isopropyl ester,

2-{2-[2-(4-fluorophenyl)ethoxy]ethyl}oxirane-2-carboxylic acid methyl ester,

2-{2-[2-(3-trifluoromethylphenyl)ethoxy]ethyl}oxirane-2-carboxylic acid sec.-butyl ester, 2-{2-[3-(3-chlorophenyl)propoxy]ethyl}oxirane-2-carboxylic acid ethyl ester, 2-{2-[3-(4-nitrophenyl)propoxy]ethyl}oxirane-2-carboxylic acid methyl ester, 2-{2-[4-(3-trifluoromethylphenyl)butoxy]ethyl}oxirane-2-carboxylic acid n-butyl ester, 2-{2-[4-(4-chlorophenyl)butoxy]ethyl}oxirane-2-carboxylic acid n-propyl ester, 2-{2-[4-(4-bromophenyl)butoxy]ethyl}oxirane-2-carboxylic acid ethyl ester, 2-[2-(3-phenylpropoxy)ethyl]oxirane-2-carboxylic acid ethyl ester, -carboxylic acid ethyl ester, 2-[2-(4-phenylbutoxy)ethyl]oxirane-2-carboxylic acid ethyl ester, 2-[3-(2-phenylethoxy)propyl]oxirane-2-carboxylic acid methyl ester, 2-[3-(3-phenylpropoxy)propyl]oxirane-2-carboxylic acid ethyl ester,
2-[3-(4-phenylbutoxy)propyl]oxirane-2-carboxylic acid n-propyl ester,
2-[4-(4-phenylbutoxy)butyl]oxirane-2-carboxylic acid ethyl ester,
2-{3-[2-(4-chlorophenyl)ethoxy]propyl}oxirane-2-carboxylic acid ethyl ester,
2-{3-[2-(3-trifluoromethylphenyl)ethoxy]propyl}oxirane-2-carboxylic acid methyl ester,
2-{3-[3-(4-nitrophenyl)propoxy]propyl}oxirane-2-carboxylic acid n-propyl ester,
2-{3-[4-(3-trifluoromethylphenyl)butoxy]propyl}oxirane-2-carboxylic acid isopropyl ester,
2-{3-[4-(4-chlorophenyl)butoxy]propyl}oxirane-2-carboxylic acid ethyl ester,
2-{4-[2-(4-chlorophenyl)ethoxy]butyl}oxirane-2-carboxylic acid n-butyl ester,
2-{4-[2-(4-fluorophenyl)ethoxy]butyl}oxirane-2-carboxylic acid methyl ester,
2-{4-[2-(3-trifluoromethylphenyl)ethoxy]butyl}oxirane-2-carboxylic acid ethyl ester,
2-{4-[3-(4-nitrophenyl)propoxy]butyl}oxirane-2-carboxylic acid ethyl ester,
2-{4-[4-(3-trifluoromethylphenyl)butoxy]butyl}oxirane-2-carboxylic acid ethyl ester,
2-{4-[4-(4-chlorophenyl)butoxy]butyl}oxirane-2-carboxylic acid ethyl ester,
2-{5-[2-(4-chlorophenyl)ethoxy]pentyl}oxirane-2-carboxylic acid methyl ester,
2-{5-[2-(3-trifluoromethylphenyl)ethoxy]pentyl}oxirane-2-carboxylic acid ethyl ester,
2-{5-[3-(4-nitrophenyl)propoxy]pentyl}oxirane-2-carboxylic acid ethyl ester,
2-{5-[3-(3-chlorphenyl)propoxy]pentyl}oxirane-2-carboxylic acid ethyl ester,
2-[5-(2-phenylethoxy)pentyl]oxirane-2-carboxylic acid n-butyl ester,
2[6-(2-phenylethoxy)hexyl]oxirane-2-carboxylic acid ethyl ester,
2-{6-[2-(4-chlorophenyl)ethoxy]hexyl}oxirane-2-carboxylic acid n-propyl ester,
2-{6-[2-(4-fluorophenyl)ethoxy]hexyl}oxirane-2-carboxylic acid methyl ester, and
2-{6-[2-(3-trifluoromethylphenyl)ethoxy]hexyl}oxirane-2-carboxylic acid ethyl ester, the corresponding oxirane-2-carboxylic acids and salts thereof with inorganic and organic bases.

Preferred representatives are 2-[4-(3-chlorophenoxy)butyl]-oxirane-2-carboxylic acid ethyl ester, 2-[4-(3-trifluoromethylphenoxy)butyl]oxirane-2-carboxylic acid ethyl ester, 2-[5-(4-chlorophenoxy)pentyl]oxirane-2-carboxylic acid ethyl ester and 2-[6-(4-chlorophenoxy)hexyl]oxirane-2-carboxylic acid ethyl ester, the corresponding oxirane-2-carboxylic acids and pharmacologically-acceptable salts thereof.

The phenalkoxyalkyl- and phenoxyalkyl-substituted oxiranecarboxylic acids of formula I and of embodiments I* and I** have a chirality center. The invention includes the racemates, the enantiomers and mixtures thereof.

The compounds according to the invention have valuable pharmacological properties which render them commercially valuable. They have a hypoglycemic and hypoketonemic action.

Because of their advantageous activity, the substituted oxiranecarboxylic acids of formula I (including embodiments I* and I**) and their pharmacologically-acceptable salts are suitable in human and veterinary medicine for the treatment and prophylaxis of illnesses based on glucose and fat metabolism disorders. Prediabetic conditions are treated for prevention of the manifestation of diabetes; manifest diabetes, for example diabetes in adults, and labile diabetes in young persons and diseases which are accompanied by an increased production of ketones are treated for control and symptom alleviation.

The invention thus also relates to a method for combating such illnesses by administration of compounds according to the invention to those subject to or afflicted with disorders of the indicated type. The invention furthermore relates to the use of compounds according to the invention in combating these illnesses.

Moreover, the invention relates to medicaments which contain one or more substituted oxiranecarboxylic acids of formula I,
wherein $R^1$ denotes a hydrogen atom (—H), a halogen atom, a lower alkyl group, a lower alkoxy group, a nitro group or a trifluoromethyl group,
$R^2$ has one of the meanings of $R^1$,
$R^3$ denotes a hydrogen atom or a lower alkyl group,
Y denotes —O—$(CH_2)_m$—,
m denotes O or an integer from 1 to 4 and
n denotes an integer from 2 to 8, with the proviso that the sum of m and n is an integer from 2 to 8,
and/or pharmacologically-acceptable salts of the acids with inorganic or organic bases.

Medicament embodiments include those which contain phenalkoxyalkyl- and phenoxyalkyl-substituted oxiranecarboxylic acids I* and I** and/or pharmacologically-acceptable salts of such acids with inorganic or organic bases.

The invention also encompasses the use of the compounds according to the invention for preparing medicaments for combating the noted illness.

The medicaments are conventionally prepared by known processes. As medicaments, the new compounds are employed as such or in combination with suitable pharmaceutical excipients. When the new pharmaceutical formulations contain pharmaceutical excipients in admixture with or in addition to one or more active compounds, the content of active compound is from 1 to 95, preferably from 15 to 85, percent by weight of the total.

According to the invention, the active compounds are used in the field of human medicine in any desired form, for example systemically, provided that sufficient levels of active compound are established and maintained in the blood or tissue. This is achieved, for example, by oral or parenteral administration in suitable doses. The pharmaceutical formulation of the active compound is advantageously in the form of unit doses appropriate for the desired mode of administration. A unit dose is, for example, in the form of a tablet, a dragee, a capsule, a suppository or a measured volume of a powder, of a granular material, of a solution, of an emulsion or of a suspension.

"Unit dose" for the purpose of the present invention means a physically-determined unit which contains an individual amount of active ingredient in combination with a pharmaceutical excipient, the content of active compound in the unit dose corresponding to a fraction or multiple of a therapeutic individual dose. An individual dose preferably contains the amount of active compound which is given in one administration and usually corresponds to a whole daily dose or a half, one-third or one-quarter of the daily dose. If only a fraction, such as a half or one-quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention contain from about 2 to 200 mg, advantageously from 10 to 100 mg and, in particular, from 20 to 60 mg of active compound.

In general, it is advantageous in human medicine to administer the active compound or compounds, when these are given orally, in a daily dose of from about 0.1 to about 30, preferably from 0.3 to 15 and, in particular, from 0.6 to 3 mg/kg of body weight, if appropriate in the form of several, preferably 1 to 3, individual administrations to achieve the desired results. An individual administration contains the active compound or compounds in amounts of from about 0.05 to about 10, preferably from 0.1 to 5 and, in particular, from 0.3 to 1 mg/kg of body weight.

Similar dosages are used in parenteral treatment, for example intravenous or intramuscular administration. From about 0.3 to 1 mg of active compound/kg of body weight is administered for this therapy.

For long-term medication, the pharmaceutical formulation is generally administered, for therapeutic purposes, at fixed points in time, such as 1 to 4 times daily, for example after each meal and/or in the evening. In acute cases, medication takes place at varying points in time. Under certain circumstances, it may be necessary to deviate from the mentioned dosages and, in particular, to do so in accordance with the nature, body weight and age of the patient being treated, the nature and severity of the illness, the frequency of administration, the nature of the formulation and of the mode of administration of the medicament, and the time or interval over which administration takes place. Thus, in some cases it may be sufficient to manage with less than the indicated amount of active compound, while such amount of active compound must be exceeded in other cases. The optimum dosage and method of administration of the active compounds required in each particular case are readily determined by the expert in accordance with his expert knowledge.

The pharmaceutical formulations ordinarily comprise one or more active compounds according to the invention and nontoxic, pharmaceutically-acceptable medicinal excipient. Excipients are used, e.g., as an admixture or diluent in solid, semi-solid or liquid form, or as a means of encasing, for example in the form of a capsule, a tablet coating, a sachet or some other container, for the therapeutically-active ingredient. An excipient serves, for example, as a promoter of the resorption of the medicament by the body, as a formulating auxiliary, as a sweetener, as a flavor correctant, as a colorant or as a preservative.

Examples of oral dosage forms are tablets, dragees, hard and soft capsules (for example, made of gelatin), dispersible powders, granules, aqueous and oily suspensions, emulsions or solutions.

Tablets contain, e.g., inert diluents, such as calcium carbonate, calcium phosphate, sodium phosphate or xylitol; granulating agents and dispersing agents, such as calcium phosphate or alginates; binders, such as starch, gelatin or gum acacia; and lubricants, such as aluminum or magnesium stearate, talc or silicone oil.

The tablets are optionally provided with a coating, such as one which brings about delayed dissolution and resorption of the medicament in the gastrointestinal tract and hence, for example, better toleration, a protracted effect or a retarded effect. Gelatin capsules optionally contain the medicament mixed with a solid diluent, for example calcium carbonate or kaolin, or an oily diluent, for example paraffin oil.

Aqueous suspensions contain, e.g., suspending agents, such as sodium carboxymethylcellulose, methylcellulose, hydroxypropylcellulose, sodium alginate, polyvinylpyrrolidone, gum tragacanth or gum acacia; dispersing agents and wetting agents, such as polyoxyethylene stearate, heptadecaethyleneoxycetanol, polyoxyethylene sorbitol monooleate, polyoxyethylene sorbitan monooleate or lecithin; preservatives, such as methyl hydroxybenzoate or propyl hydroxybenzoate; flavoring agents; and sweeteners, such as saccharin or sodium cyclamate.

Oily suspensions contain, for example, paraffin oil, and thickeners, such as beeswax, hard paraffin or cetyl alcohol; and furthermore sweeteners, flavoring agents and antioxidants.

Water dispersible powders and granules contain the medicaments mixed, e.g., with dispersing agents, wetting agents and suspending agents, for example those previously mentioned, as well as sweeteners, flavoring agents and colorants.

Emulsions contain, for example, paraffin oil in addition to emulsifying agents, such as gum acacia, gum tragacanth, phosphatides, sorbitan monooleate or polyoxyethylene sorbitan monooleate, and sweeteners and flavoring agents.

For parenteral administration of the medicaments, sterile injectable aqueous suspensions, isotonic salt solutions or other solutions, which optionally contain dispersing agents or wetting agents and/or pharmacologically-acceptable diluents, for example propylene glycol or butylene glycol, are used.

The active compound or compounds are also optionally prepared in a micro-encapsulated form, if appropriate together with one or more of the noted excipients or additives.

In addition to the phenalkoxyalkyl- and phenoxyalkyl-substituted oxiranecarboxylic acids according to the invention and/or their salts, the pharmaceutical formulations alternatively contain one or more pharmacologically-active ingredients from other groups of medicaments, such as antidiabetic agents (sulfonamides and sulfonylureas), for example carbutamide, tolbutamide, clorpropamide, glibenclamide, glibornuride, glisoxepide, gliquidone and glymidine, or hypolipidaemic agents, such as nicotinic acid and derivatives and salts thereof.

The invention also relates to a process for preparing phenalkoxyalkyl- and phenoxyalkyl-substituted oxiranecarboxylic acids of formula I and salts of the acids, characterized by oxidizing substituted α-methylenecarboxylic acids of the formula

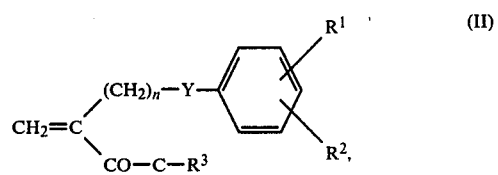
(II)

wherein $R^1$, $R^2$, $R^3$, Y and n have their previously-ascribed meanings, and optionally saponifying the resulting lower alkyl esters or optionally converting the resulting acids into salts or lower alkyl esters.

The oxidation of the α-methylenecarboxylic acids II is effected under known and well-established conditions for oxidation of carbon-carbon double bonds to obtain epoxides. Suitable oxidizing agents include peroxo compounds, such as hydrogen peroxide, peracetic acid, trifluoroperacetic acid, 3,5-dinitroperbenzoic acid and, preferably, m-chloroperbenzoic acid. The reaction is appropriately carried out in inert solvent, for example an aromatic or chlorinated hydrocarbon, such as benzene, toluene, methylene chloride or chloroform. The reaction temperature is between 0° C. and the boiling point of the solvent, preferably between 20° and 70° C.

The saponification of lower alkyl esters is also effected conventionally. It is carried out, for example, with an aqueous or alcoholic (for example ethanolic) alkali-metal hydroxide (for example potassium hydroxide) solution at room temperature, optionally with the inclusion of an inert diluent, such as dioxane, tetrahydrofurane, or toluene.

The conversion of acids of formula I ($R^3=$—H) or of embodiments I* and I** into salts is effected, e.g., by direct alkaline hydrolysis of the acid derivatives I ($R^3=$lower alkyl). That inorganic or organic base of which the salt is desired is used as the alkaline reactant. The salts are alternatively obtained by reacting the acids I ($R^3=$—H) with the stoichiometric equivalent of the corresponding base, for example sodium hydroxide or sodium ethanolate, by converting readily-soluble salts into sparingly-soluble salts by double decomposition or by converting any salt into a pharmacologically-acceptable salt.

The conversion of oxiranecarboxylic acids of formula I ($R^3=$—H) or of embodiments I* and I** into corresponding lower alkyl esters ($R^3=$lower alkyl) is effected in a well-established manner. For example, they are esterified (a) with a lower alkanol in a reaction medium comprising strong acid, such as sulfuric acid or p-toluenesulfonic acid, or acid ion exchanger under conditions in which no decarboxylation takes place or (b) with dialkylsulfate or an alkyl halide in a reaction medium comprising diazabicycloundecene or diazabicyclononene in inert solvent, such as benezene, toluene or acetone.

The compounds of the general formula I are normally obtained in the form of racemic mixtures which, by means of known processes, are separated into the enantiomers. For example, the racemate is converted with an optically-active splitting agent into diastereoisomers which subsequently are separated by selective crystallization and converted into the appropriate optical isomers. Suitable optically-active splitting agents include, e.g., optically-active bases, such as l- and d-l-phenylethyl amine, cinchonidine or d-ephedrine, from which salts of the acids of formula I are prepared, or optically-active alcohols, such as borneol or menthol, from which esters of the acids of formula I are prepared. The racemic mixtures are also separated by chromatography via optically-active sorbing agents. Alternatively, the α-methylenecarboxylic acids II are primarily reacted with an optically-active splitting agent, e.g. borneol or menthol; the obtained products are subsequently oxidized to the mixtures of the diastereoisomers of the oxiranecarboxylic acid esters, from which the optical isomers of the acids I are obtained in a manner known to the expert.

α-Methylenecarboxylic acids of formula II, wherein $R^1$, $R^2$, $R^3$, Y and n have their respective meanings for embodiments I* and I**, are employed for preparing the substituted oxiranecarboxylic acids of embodiments I* and I**.

The α-methylenecarboxylic acids of formula II are prepared by conventional methods from known starting materials. They are valuable intermediate products for the synthesis of the oxiranecarboyxlic acids I, I* and I**.

The α-methylenecarboxylic acids II are prepared, for example, by a process analogous to that of H. Stetter and H. Kuhlmann [Synthesis, 1979, 29] by reacting a malonic acid half-ester of the formula

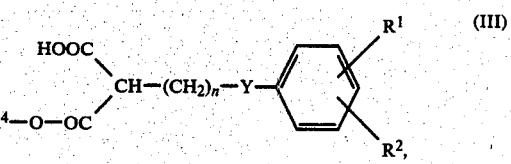

wherein $R^1$, $R^2$, Y and n have their previously-indicated meanings and $R^4$ denotes a lower alkyl group, with formaldehyde in a reaction medium comprising pyridine and secondary amine, preferably piperidine, and optionally saponifying the lower alkyl esters obtained.

The malonic half-esters III are prepared by methods with which those skilled in the art are familiar, for example by reacting dialkyl malonates IV with phenalkoxyalky or phenoxyalkyl compounds V and partially hydrolyzing the resulting malonic acid diesters VI, according to the following reaction scheme:

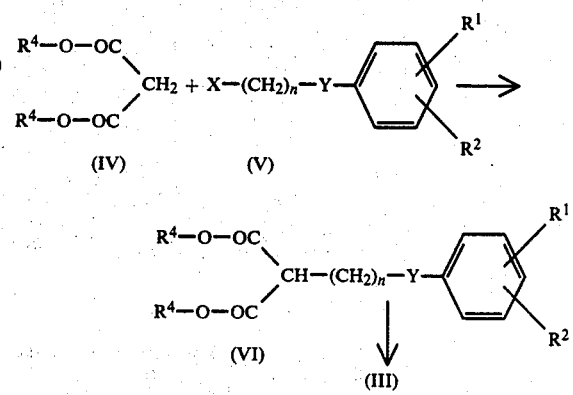

wherein
$R^1$, $R^2$, $R^4$, Y and n have their previously-noted meanings and
X denotes a leaving group, for example a chlorine or bromine atom or a mesyloxy or p-toluenesulfonyloxy group.

Appropriate starting compounds III* or III**; IV* or IV**; V* or V**; and VI* or VI** (in which $R^1$, $R^2$, Y and n have the meanings corresponding to those for embodiments I* and I**, respectively, and $R^{4*}$ denotes a lower alkyl group, and $R^{4**}$ denotes a methyl or ethyl group, and X* and X**, respectively, denote a chlorine or bromine atom or a mesyloxy- or p-toluenesulfonyloxy group) are employed for the preparation of α-methylenecarboxylic acids II* and II**.

The phenalkoxyalkyl and phenoxyalkyl compounds V and their embodiments V* and V**, respectively, are prepared by methods known to the artisan, e.g. in analogy to J. Augstein et al., [J. Med. Chem., 8 (1965) 356 to 367] or J. D. Genzer et al., [J. Amer. Chem. Soc., 73 (1951) 3159 to 3162] or Sh. Mamedov et al. [Chem. Abstr., 59 (1963) 4401e and Chem. Abstr., 60 (1964) 5321c].

The phenalkoxyalkyl and phenoxyalkyl compounds V are prepared, for example, analogously to Genzer et al. by reacting alkanediols VII with phenalkyl chlorides VIII and reacting the resulting phenalkoxy alkanols IX with thionyl halides or sulfonic acid halides, according to the following reaction scheme:

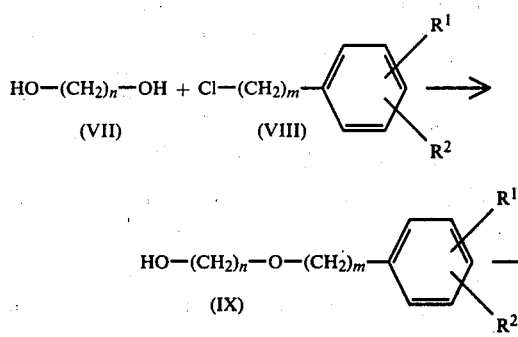

wherein $R^1$, $R^2$ and n have their previously-noted meanings and m denotes an integer from 1 to 4.

The phenalkyl chlorides VIII are prepared by methods with which those skilled in the art are familiar, by reducing carboxylic acids X and reacting the resulting alkanols XI with thionyl chloride, according to the following reaction scheme:

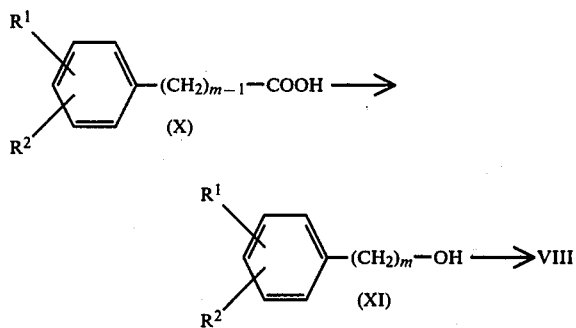

wherein $R^1$ and $R^2$ have their previously-noted meanings and m denotes an integer from 1 to 4.

The following Examples, wherein b.p. denotes boiling point and m.p. denotes melting point, illustrate the invention without limiting it. The temperature data are in °C.

EXAMPLE 1

2-(4-Phenoxybutyl)oxirane-2-carboxylic acid ethyl ester (a) 2-(4-Phenoxybutyl)oxirane-2-carboxylic acid ether ester -

32 g of 2-methylene-6-phenoxyhexanoic acid ethyl ester and 78.5 g of m-chloroperbenzoic acid (85% pure) are boiled under reflux in 200 ml of methylene chloride for 24 hours. The mixture is allowed to cool, the m-chloroperbenzoic acid which has separated out is filtered off and washed thoroughly with petroleum ether. The combined filtrates are concentrated, the oily reddish-brown residue is taken up in 150 ml of acetone, 100 ml of saturated sodium bicarbonate solution and 100 ml of water are added, and the mixture is stirred for 30 minutes. The mixture is then extracted 3 times with 500 ml of petroleum ether each time, the organic phase is concentrated, and the reddish-brown residue is distilled. The fraction boiling between 113° and 140° C. (0.008 mm Hg=1.06 Pa) is chromatographed on silica gel (eluant: petroleum ether/ethyl acetate 9:1) and distilled again. 6.15 g of the title compound [b.p. 125° under 0.07 mm Hg (9.3 Pa)] are obtained.

(b) 2-Methylene-6-phenoxyhexanoic acid ethyl ester- 66.45 g of 4-phenoxybutylmalonic acid ethyl ester, 45 ml of pyridine, 3 ml of piperidine and 9.9 g of paraformaldehyde are stirred together at 50° C. for 4 hours. After cooling, 400 ml of water are added to the reaction mixture which is then acidified with half-concentrated hydrochloric acid, while cooling with ice. The reaction mixture is then extracted 3 times with 200 ml of diethyl ether each time, the combined organic phases are concentrated and distilled in vacuo. 43.6 g 2-methylene-6-phenoxyhexanoic acid ethyl ester are obtained as a colorless liquid of b.p. 140° C. under 0.06 mm Hg (9 Pa).

(c) 4-Phenoxybutylmalonic acid ethyl ester -

A solution of 16.1 g of potassium hydroxide in 250 ml of ethanol is added dropwise to 87 g of 4-phenoxybutylmalonic acid diethyl ester in 250 ml of ethanol at room temperature. The mixture is stirred for 24 hours and substantially concentrated in vacuo; the residue is taken up in 500 ml of water and the aqueous mixture is extracted with 200 ml of diethyl ether. The aqueous phase is acidified with concentrated hydrochloric acid, while cooling with ice, and extracted 3 times with 200 ml of diethyl ether each time. After drying over sodium sulfate, the organic phase is concentrated. 66.45 g of 4-phenoxybutylmalonic acid ethyl ester of m.p. 69° to 72° C. are obtained.

EXAMPLE 2

2-[4-(4-Methylphenoxy)butyl]oxirane-2-carboxylic acid ethyl ester (a) 2-[4-(4-Methylphenoxy)butyl]oxirane-2-carboxylic acid ethyl ester -

23.3 g of the title compound [pale yellow oil which is purified by chromatography on silica gel (eluant: petroleum ether/methylene chloride 1:1)] are obtained from 116.6 g of 6-(4-methylphenoxy)-2-methylenehexanoic acid ethyl ester and 152.2 g of m-chloroperbenzoic acid by the procedure described in Example 1a), 41.8 g of the starting compound are regained.

(b) 6-(4-Methylphenoxy)-2-methylenehexanoic acid ethyl ester -

166.6 g of 6-(4-methylphenoxy-2-methylenehexanoic acid ethyl ester [b.p. 132° to 134° C. under 0.1 mm Hg (13.3 Pa)] are obtained from 254 g of 4-(4-methylphenoxy)butylmalonic acid ethyl ester, 27.2 g of paraformaldehyde, 260 ml of pyridine and 9 ml of piperidine by the procedure described in Example 1b).

(c) 4-(4-Methylphenoxy)butylmalonic acid ethyl ester -

254.2 of 4-(4-methylphenoxy)butylmalonic acid ethyl ester (pale yellow oil) are obtained from 303.7 g 44-methylphenoxy)butylmalonic acid diethyl ester and 60.8 g of potassium hydroxide in 1.5.1 of ethanol by the procedure described in Example 1c).

(d) 4-(4-Methylphenoxy)butylmalonic acid diethyl ester -

176.2 g of malonic acid diethyl ester are added dropwise at 50° C. to a sodium ethylate solution freshly prepared from 23 g of sodium and 500 ml of ethanol. The mixture is kept at this temperature for 2 hours, and 243.2 g of 4-(4-methylphenoxy)butyl bromide are then added dropwise. When the addition is complete, the obtained mixture is stirred at 60° C. for 3 hours, and substantially concentrated; 1 l of ice-water is then added and the mixture is extracted 3 times with a total of 1 liter of methylene chloride. The combined organic phases are dried over sodium sulfate, and the solvent and the excess malonic acid diethyl ester is distilled off in vacuo. 303.9 g of 4-(4-methylphenoxy)butylmalonic acid diethyl ester are obtained as pale yellow, oily residue.

EXAMPLE 3

2-[4-(3-Trifluoromethylphenoxy)butyl]oxirane-2-carboxylic acid ethyl ester (a) 2-[4-(3-Trifluoromethylphenoxy)butyl]oxirane-2-carboxylic acid ethyl ester -

46.9 g of the title compound [colorless oil, purified by chromatography on silica gel (eluant: petroleum ether/methylene chloride 1:1] are obtained from 48.3 g of 2-methylene-6-(3-trifluoromethylphenoxy)hexanoic acid ethyl ester and 62 g of m-chloroperbenzoic acid in 950 ml of methylene chloride by the procedure described in Example 1a).

(b) 2-Methylene-6-(3-trifluoromethylphenoxy)hexanoic acid ethyl ester -

58.7 g of 2-methylene-6-(3-trifluoromethylphenoxy)hexanoic acid ethyl ester [colorless oil, purified by chromatography on silica gel (eluant: petroleum ether/methylene chloride 1:1] are obtained from 90.7 g of 4-(3-trifluoromethylphenoxy)butylmalonic acid ethyl ester, 8.3 g of paraformaldehyde, 95 ml of pyridine and 2.5 ml of piperidine by the procedure described in Example 1b).

(c) 4-(3-Trifluoromethylphenoxy)butylmalonic acid ethyl ester -

90.7 g of 4-(3-trifluoromethylphenoxy)butylmalonic acid ethyl ester (yellowish, viscous oil) are obtained from 117 g of 4-(3-trifluoromethylphenoxy)butylmalonic acid diethyl ester and 20.5 g of potassium hydroxide in 650 ml of ethanol by the procedure described in Example 1c).

(d) 4-(3-Trifluoromethylphenoxy)butylmalonic acid diethyl ester -

117.4 g of 4-(3-trifluoromethylphenoxy)butylmalonic acid diethyl ester (light oil) are obtained from 102.4 g of 4-(3-trifluoromethylphenoxy)butyl bromide, 58 g of malonic acid diethyl ester and a solution of 8 g sodium in 280 ml of ethanol by the procedure described in Example 2d).

(e) 4-(3-Trifluoromethylphenoxy)butyl bromide -

267 ml of 1.6 N sodium hydroxide solution are added dropwise with stirring at 100° C. within 90 minutes to a mixture of 69.3 g of 3-hydroxybenzotrifluoride and 119 g of 1,4-dibromobutane. The mixture is stirred at this temperature for a further 5 hours and is then allowed to cool. 200 ml of methylene chloride are added, the organic phase is separated off, washed with dilute sodium hydroxide solution, dried over sodium sulfate and concentrated. The residue is distilled in vacuo. 102.6 g of 4-(3-trifluoromethylphenoxy)butyl bromide of b.p. 143° to 144° C. (13 mm Hg=1730 Pa) are obtained.

EXAMPLE 4

2-[4-(3-Chlorophenoxy)butyl]oxirane-2-carboxylic acid ethyl ester (a) 2-[4-(3-Chlorophenoxy)butyl]oxirane-2-carboxylic acid ethyl ester -

50.7 g of the title compound [colorless oil of b.p. 135° to 136° C. at 0.05 mm Hg (6.7 Pa)] are obtained from 110.2 g of 6-(3-chlorophenoxy)-2-methylenehexanoic acid ethyl ester and 135.5 g of m-chloroperbenzoic acid in 1.4 l of methylene chloride by the procedure described in Example 1a).

(b) 6-(3-Chlorophenoxy)-2-methylenehexanoic acid ethyl ester -

110.6 g of 6-(3-chlorophenoxy)-2-methylenehexanoic acid ethyl ester [b.p. 131° to 134° C. at 0.1 mm Hg (13.3 Pa)] are obtained from 178 g of 4-(3-chlorophenoxy)butylmalonic acid ethyl ester, 17.8 g of paraformaldehyde, 180 ml of pyridine and 5.6 ml of piperidine by the procedure described in Example 1b).

(c) 4-(3-Chlorophenoxy)butylmalonic acid ethyl ester -

178.2 g of 4-(3-chlorophenoxy)butylmalonic acid ethyl ester (pale yellow oil) are obtained from 231.5 g of 4-(3-chlorophenoxy)butylmalonic acid diethyl ester and 43.6 g of potassium hydroxide in 1.05 l of ethanol by the procedure described in Example 1c).

(d) 4-(3-Chlorophenoxy)butylmalonic acid diethyl ester -

231.7 g of 4-(3-chlorophenoxy)butylmalonic acid diethyl ester (pale yellow oil) are obtained from 186.9 g of 4-(3-chlorophenoxy)butyl bromide, 124.9 g of malonic acid diethyl ester and a solution of 16.3 g sodium in 650 ml of ethanol by the procedure described in Example 2d).

EXAMPLE 5

2-(2-Phenoxyethyl)oxirane-2-carboxylic acid ethyl ester (a) 2(2-Phenoxyethyl)oxirane-2-carboxylic acid ethyl ester -

9.3 g of the title compound [almost colorless oil, purified by chromatography on silica gel (eluant: methylene chloride] are obtained from 25.4 g of 2-methylene-4-phenoxybutyric acid ethyl ester and 43.7 g of m-chloroperbenzoic acid in 500 ml of methylene chloride by the procedure described in Example 1a).

(b) 2- Methylene-4-phenoxybutyric acid ethyl ester -

62.5 g of 2-methylene-4-phenoxybutyric acid ethyl ester [colorless oil of b.p. 97° to 100° C. at 0.01 mm Hg (1.3 Pa)] are obtained from 94.5 g of 2-phenoxyethylmalonic acid ethyl ester, 11.8 g of paraformaldehyde, 95 ml of pyridine and 3.8 ml of piperidine by the procedure described in Example 1b).

(c) 2-Phenoxyethylmalonic acid ethyl ester -

94.5 g of 2-Phenoxyethylmalonic acid ethyl ester are obtained from 147 g of 2-phenoxyethylmalonic acid diethyl ester and 28.1 g of potassium hydroxide in 800 ml of ethanol by the procedure described in Example 1c).

EXAMPLE 6

2-(3-Phenoxypropyl)oxirane-2-carboxylic acid ethyl ester (a) 2-(3-Phenoxypropyl)oxirane-2-carboxylic acid ethyl ester -

14.0 g of the title compound [almost colorless oil, purified by chromatography on silica gel (eluant: methylene chloride)] are obtained from 70.3 g of 2-methylene-5-phenoxyvaleric acid ethyl ester and 124.3 g of m-chloroperbenzoic acid in 900 ml of methylene chloride by the procedure described in Example 1a).

(b) 2-Methylene-5-phenoxyvaleric acid ethyl ester -

142.4 g of 2-methylene-5-phenoxyvaleric acid ethyl ester [b.p. 108° to 111° C. at 0.01 mm Hg (1.3 Pa)] are obtained from 200.6 g of 2-phenoxypropylmalonic acid ethyl ester, 23.8 g of paraformaldehyde, 200 ml of pyridine and 7.6 ml of piperidine by the procedure described in Example 1b).

(c) 3-Phenoxypropylmalonic acid ethyl ester -

200.6 g of 3-phenoxypropylmalonic acid ethyl ester (yellow oil) are obtained from 302 g of 3-phenoxypropylmalonic acid diethyl ester and 52.2 g of potassium hydroxide in 1.2 of ethanol by the procedure described in Example 1c).

EXAMPLE 7

2-[6-(4-Chlorophenoxy)hexyl]oxirane-2-carboxylic acid ethyl ester (a) 2-[6-(4-Chlorophenoxy)hexyl]oxirane-2-carboxylic acid ethyl ester -

5.5 g of the title compound [colorless oil of b.p. 164° C. at 0.2 mm Hg (26.6 Pa)] are obtained from 15.0 g of 8-(4-chlorophenoxy)-2-methyleneoctanoic acid ethyl ester and 14.72 g m-chloroperbenzoic acid in 50 ml of methylene chloride by the procedure described in Example 1a).

(b) 8-(4-Chlorophenoxy)-2-methyleneoctanoic acid ethyl ester -

52.1 g of 8-(4-chlorophenoxy)-2-methyleneoctanoic acid ethyl ester [b.p. 171° C. at 0.1 mm Hg (13.3 Pa)] are obtained from 74 g of 6-(4-chlorophenoxy)hexylmalonic acid ethyl ester, 8.2 g of paraformaldehyde, 41 ml of pyridine and 2.8 ml of piperidine by the procedure described in Example 1b).

(c) 6-(4-chlorophenoxy)hexylmalonic acid ethyl ester (yellowish viscous oil) are obtained from 83.5 g of 6-(4-chlorophenoxy)hexylmalonic acid diethyl ester and 14.4 g of potassium hydroxide in 500 ml of ethanol by the procedure described in Example 1c).

(d) 6-(4-Chlorophenoxy)hexylmalonic acid diethyl ester -

87 g of 6-(4-chlorophenoxy)hexylmalonic acid diethyl ester [b.p. 173° C. at 0.1 mm Hg (13.3 Pa)] are obtained from 106.7 g of 6-(4-chlorophenoxy)hexyl bromide, 53.8 g of malonic acid diethyl ester and a solution of 8.4 g of sodium in 350 ml of ethanol by the procedure described in Example 2d).

EXAMPLE 8

2-[3-(4-Nitrophenoxy)propyl]oxirane-2-carboxylic acid ethyl ester (a) 2-[3-(4-Nitrophenoxy)propyl]oxirane-2-carboxylic acid ethyl ester -

3.8 g of the title compound (yellow oil) are obtained from 10.0 g of 2-methylene-5-(4-nitrophenoxy)valeric acid ethyl ester and 10.5 g of m-chloroperbenzoic acid in 50 ml of methylene chloride by the procedure described in Example 1a).

(b) 2-Methylene-5-(4-nitrophenoxy)valeric acid ethyl ester -

61 g of 2-methylene-5-(4-nitrophenoxy)valeric acid ethyl ester [yellow oil of b.p. 167° to 170° C. at 0.005 mm Hg (0.7 Pa)] are obtained from 89 g of 3-(4-nitrophenoxy)propylmalonic acid ethyl ester, 10.8 g of paraformaldehyde, 54 ml of pyridine and 4 ml of piperidine by the procedure described in Example 1b).

(c) 3-(4-Nitrophenoxy)propylmalonic acid ethyl ester 90 g of 3-(4-nitrophenoxy)propylmalonic acid ethyl ester (yellow oil) are obtained from 116.5 g of 3-(4-nitrophenoxy)propylmalonic acid diethyl ester and 21.7 g of potassium hydroxide in 500 ml of ethanol by the procedure described in Example b 1c).

(d) 3-(4-Nitrophenoxy)propylmalonic acid diethyl ester -

119.5 g of 4-(4-nitrophenoxy)propylmalonic acid diethyl ester (yellowish oil) are obtained from 110.5 g of 3-(4-nitrophenoxy)propyl bromide, 101 g of malonic acid diethyl ester and a solution of 9.7 g of sodium in 1.1 l of ethanol by the procedure described in Example 2d).

EXAMPLE 9

2-(5-Phenoxypentyl)oxirane-2-carboxylic acid ethyl ester (a) 2-(5-Phenoxypentyl)oxirane-2-carboxylic acid ethyl ester -

2.15 g of the title compound [colorless oil, purified by chromatography on silica gel (eluant: petroleum ether-/ethyl acetate 9:1] are obtained from 10 g of 2-methylene-7-phenoxyheptanoic acid ethyl ester and 11.6 g of m-chloroperbenzoic acid in 50 ml of methylene chloride by the procedure described in Example 1a). 4.7 g of the starting compound are regained.

(b) 2-Methylene-7-phenoxyheptanoic acid ethyl ester -

58 g of 2-methylene-7-phenoxyheptanoic acid ethyl ester [b.p. 118° C. at 0.001 mm Hg (0.13 Pa)] are obtained from 143.7 g of 5-phenoxypentylmalonic acid ethyl ester, 18.3 g of paraformaldehyde, 92 ml of pyridine and 6 ml of piperidine by the procedure describe in Example 1b).

(c) 5-Phenoxypentylmalonic acid ethyl ester -

143.7 g of 5-phenoxypentylmalonic acid ethyl ester (yellowish oil) are obtained from 174.4 g of 5-phenoxypentylmalonic acid diethyl ester and 34.4 g of potassium hydroxide in 500 ml of ethanol by the procedure described in Example 1c).

EXAMPLE 10

2-[5-(4-Chlorophenoxy)pentyl]oxirane-2-carboxylic acid ethyl ester (a) 2-[5-(4-Chlorophenoxy)pentyl]oxirane-2-carboxylic acid ethyl ester- 6.6 g of the title compound [b.p. 176° to 178° C. at 0.005 mm Hg (0.7 Pa)] are obtained from 10 g of 7-(4-chlorophenoxy)-2-methyleneheptanoic acid ethyl ester and 10.9 g of m-chloroperbenzoic acid in 50 ml of methylene chloride by the procedure described in Example 1a).

(b) 7-(4-Chlorophenoxy)-2-methyleneheptanoic acid ethyl ester- 88.6 g of 7-(4-chlorophenoxy)-2-methyleneheptanoic acid ethyl ester [b.p. 154° C. at 0.01 mm Hg (1.3 Pa)] are obtained from 202.5 g of 5-(4-chlorophenoxy)pentylmalonic acid ethyl ester, 23.4 g of paraformaldehyde, 116 ml of pyridine and 7.9 ml of piperidine by the procedure described in Example 1b).

(c) 5-(4-Chlorophenoxy)pentylmalonic acid ethyl ester- 202.5 g of 5-(4-chlorophenoxy)pentylmalonic acid ethyl ester (viscous oil) are obtained from 250.6 g of 5-(4-chlorophenoxy)pentylmalonic acid diethyl ester and 44.6 g of potassium hydroxide in 500 ml of ethanol by the procedure described in Example 1c).

(d) 5-(4-Chlorophenoxy)pentylmalonic acid diethyl ester- 265 g of 5-(4-chlorophenoxy)pentylmalonic acid diethyl ester [of b.p. 160° to 161° C. at 0.01 mm Hg (1.3 Pa)] are obtained from 212.6 g of 5-(4-chlorophenoxy)pentyl bromide, 185.8 g of malonic acid diethyl ester and a solution of 17.7 g of sodium in 1.25 l of ethanol by the procedure described in Example 2d).

EXAMPLE 11

2-(3-Benzyloxypropyl)oxirane-2-carboxylic acid ethyl ester (a) 2-(3-Benzyloxypropyl)oxirane-2-carboxylic acid ethyl ester- 7.2 g of the title compound [almost colorless oil, purified by chromatography on silica gel (eluant: petroleum ether/ethyl acetate 9:1)] are obtained from 26 g of 5-benzyloxy-2-methylenevaleric acid ethyl ester and 48 g of m-chloroperbenzoic acid in 200 ml of methylene chloride by the procedure described in Example 1a).

(b) 5-Benzyloxy-2-methylenevaleric acid ethyl ester- 30.1 g of 5-benzyloxy-2-methylenevaleric acid ethyl ester [yellowish oil, purified by chromatography on silica gel (eluant: petroleum ether/ethyl acetate 9:1)] are obtained from 44 g of 3-benzyloxypropylmalonic acid ethyl ester, 30 ml of pyridine, 2 ml of piperidine and 6.6 g of paraformaldehyde by the procedure described in Example 1b).

(c) 3-Benzyloxypropylmalonic acid ethyl ester- 44.5 g of 3-benzyloxypropylmalonic acid ethyl ester (tough, yellowish oil) are obtained from 67 g of 3-benzyloxypropylmalonic acid diethyl ester and 12.4 g of potassium hydroxide in 200 ml of ethanol by the procedure described in Example 1c).

(d) 3-Benzyloxypropylmalonic acid diethyl ester- 67.4 g of 3-benzyloxypropylmalonic acid diethyl ester (yellowish oil) are obtained from 86 g of 3-benzyloxypropyl bromide, 78 g of malonic acid diethyl ester and a solution of 9 g of sodium in 600 ml of ethanol by the procedure described in Example 2d).

EXAMPLE 12

2-[5-(4-Chlorophenoxy)pentyl]oxirane-2-carboxylic acid 2.0 g of 2-[5-(4-chlorophenoxy)pentyl]oxirane-2-carboxylic acid ethyl ester, 6.4 ml of 1 N sodium hydroxide solution and 6.4 ml of tetrahydrofuran are stirred at room temperature until a clear solution has formed (after about one hour). The solution is concentrated to one half of its volume in vacuo and 6.5 ml of 1 N hydrochloric acid are added while cooling with ice. The resulting mixture is extracted 3 times with 20 ml of diethyl ether each time. After drying the combined organic phases over sodium sulfate and evaporating off the solvent 1.65 g of the title compound as a viscous oil are obtained.

EXAMPLE 13

Sodium 2-[4-(3-trifluoromethylphenoxy)butyl]oxirane-2-carboxylate 4.0 g of 2-[4-(3-trifluoromethylphenoxy)butyl]oxirane-2-carboxylic acid ethyl ester, 12 ml of 1 N sodium hydroxide solution and 16 ml of tetrahydrofuran are stirred for 2 hours at room temperature. The solution which has formed is concentrated to one half of its volume in vacuo and is then extracted 2 times with 50 ml of diethyl ether each time. On standing a precipitate crystallizes out of the aqueous solution, which is filtered off and washed with little water and diethyl ether. 2.44 g of the title compound of m.p. 94° to 97° C. are obtained by gradual concentration of the filtrates to a small volume.

EXAMPLE 14

Sodium 2-[4-(3-chlorophenoxy)butyl]oxirane-2-carboxylate 11.4 g of the title compound of m.p. 102° to 106° C. are obtained analogously to Example 13 from 13.1 g of 2-[4-(3-chlorophenoxy)butyl]oxirane-2-carboxylic acid ethyl ester and 43.8 ml of 1 N sodium hydroxide solution in 50 ml of tetrahydrofuran.

EXAMPLE 15

Calcium 2-[4-(3-chlorophenoxy)butyl]oxirane-2-carboxylate 400 mg of calcium chloride in 5 ml of water are added to a solution of 1 g of sodium 2-[4-(3-chlorophenoxy)butyl]oxirane-2-carboxylate in 10 ml of water. The greasy residue which has formed is separated off by decantation, and the sediment is washed by two decantations with little water. The residue is dried over phosphorus pentoxide. 840 mg of the title compound are obtained. Decomposition (without melting) at 225° C.

EXAMPLE 16

2-[4-(3-Trifluoromethylphenoxy)butyl]oxirane-2-carboxylic acid methyl ester 5.4 g of the title compound [colorless oil, purified by chromatography on silica gel (eluant: petroleum ether/methylene chloride 1:1)] are obtained from 7.8 g of 2-methylene-6-(3-trifluoromethylphenoxy)hexanoic acid methyl ester and 11.0 g of m-chloroperbenzoic acid by the procedure described in Example 3a).

8.0 g of the starting compound 2-methylene-6-(3-trifluoromethylphenoxy)hexanoic acid methyl ester are obtained from 17.5 g of 4-(3-trifluoromethylphenoxy)butylmalonic acid dimethyl ester by the procedure described in Example 3b) and 3c).

EXAMPLE 17

2-[2-(3-Phenylpropyloxy)ethyl]oxirane-2-carboxylic acid ethyl ester (a) 2-[2-(3-Phenylpropyloxy)ethyl]oxirane-2-carboxylic acid ethyl ester- 6.6 g of the title compound [colorless oil, purified by chromatography on silica gel (eluant: petroleum ether/ethyl acetate 9:1]are obtained from 18.0 g of 2-methylene-4-(3-phenylpropyloxy)butyric acid ethyl ester and 22 g of m-chloroperbenzoic acid in 150 ml of methylene chloride by the procedure described in Example 1a).

(b) 2-methylene-4-(3-phenylpropyloxy)butyric acid ethyl ester- 27 g of 2-methylene-4-(3-phenylpropyloxy)butyric acid ethyl ester [colorless oil of b.p. 140° C. at 0.1 mm Hg (13 Pa)] are obtained from 45 g of 2-(3-phenylpropyloxy)ethylmalonic acid ethyl ester, 28.5 ml of pyridine, 1.9 ml of piperidine and 5.74 g of paraformaldehyde by the procedure described in Example 1b).

(c) 2-(3-Phenylpropyloxy)ethylmalonic acid ethyl ester- 46.6 g of 2-(3-phenylpropyloxy)ethylmalonic acid ethyl ester (yellowish oil) are obtained from 54 g of 2-(3-phenylpropyloxy)-ethylmalonic acid diethyl ester and 10.68 g of potassium hydroxide in 120 ml of ethanol by the procedure described in Example 1c).

(d) 2-(3-Phenylpropyloxy)ethylmalonic acid diethyl ester- 54 g of 2-(3-phenylpropyloxy)ethylmalonic acid diethyl ester] b.p. 168° to 171° C. at 0.2 mm Hg (27 Pa)] are obtained from 72.7 g of 2-(3-phenylpropyloxy)ethyl chloride, 87.9 g of malonic acid diethyl ester, 3 g of potassium iodide and a solution of 12.6 g of sodium in 300 ml of ethanol by the procedure described in Example 2d).

EXAMPLE 18

2-[2-(4-Chlorobenzyloxy)ethyl]oxirane-2-carboxylic acid ethyl ester (a) 2-[2-(4-chlorobenzyloxy)ethyl]oxirane-2-carboxylic acid ethyl ester- 6.2 g of the title compound [b.p. 130° to 135° C. at 0.05 mm Hg (7 Pa)] are obtained from 10.3 g of 4-(4-chlorobenzyloxy)-2-methylenebutyric acid ethyl ester and 13 g of m-chloroperbenzoic acid in 100 ml of methylene chloride by the procedure described in Example 1a).

(b) 4-(4-Chlorobenzyloxy)-2-methylenebutyric acid ethyl ester- 14.0 g of 4-(4-chlorobenzyloxy)-2-methylenebutyric acid ethyl ester [b.p. 125° to 130° C. at 0.1 mm Hg (13.3 Pa)] are obtained from 19.0 g of 2-(4-chlorobenzyloxy)ethylmalonic acid ethyl ester, 12 ml of pyridine, 0.8 ml of piperidine and 2.0 g of paraformaldehyde by the procedure described in Example 1b).

(c) 2-(4-Chlorobenzyloxy)ethylmalonic acid ethyl ester- 19.5 g of 2-(4-chlorobenzyloxy)ethylmalonic acid ethyl ester are obtained from 26.0 g of 2-(4-chlorobenzyloxy)ethylmalonic acid diethyl ester and 5.05 g of potassium hydroxide in 100 ml of ethanol by the procedure described in Example 1c).

(d) 2-(4-Chlorobenzyloxy)ethylmalonic acid diethyl ester- 60.3 g of 2-(4-chlorobenzyloxy)ethylmalonic acid diethyl ester [b.p. 168° C. at 0.2 mm Hg (27 Pa)] are obtained from 87 g of 2-(4-chlorobenzyloxy)ethyl chloride, 102 g of malonic acid diethyl ester, 3 g of potassium iodide and a solution of 14.6 g of sodium in 300 ml of ethanol by the procedure described in Example 2d).

EXAMPLE 19

Batch for ampoules 100 g of 2-[5-(4-Chlorophenoxy)pentyl]oxirane-2-carboxylic acid are dissolved in about 8 liters of doubly-distilled water, the equivalent amount of sodium hydroxide solution being added. The solution is adjusted to pH 7.0±0.5 and made up to 10 liters with doubly-distilled water. It is then filtered under sterile conditions and filled into 2 ml ampoules under germ-free conditions.

EXAMPLE 20

10,000 capsules with an active compound content of 30 mg are prepared from the following constitutents:

300 g of 2-(5-phenoxypentyl)oxirane-2-carboxylic acid ethyl ester are mixed with 500 g of neutral oil, and the mixture is filled into soft gelatin capsules.

EXAMPLE 21

1,000 capsules with an active compound content of 25 mg are prepared as follows:

25 g of 2-[4-(3-chlorophenoxy)butyl]oxirane-2-carboxylic acid ethyl ester are dissolved in 100 ml of methylene chloride The solution is mixed thoroughly with 75 g of micronized silicic acid. The mixture is evaporated to dryness and then filled into hard gelatin capsules.

EXAMPLE 22

10,000 capsules with an active compound content of 20 mg are prepared as follows:

200 g of 2-[4-(3-trifluoromethylphenoxy)butyl]oxirane-2-carboxylic acid ethyl ester are dissolved in 1,000 ml of methylene chloride. The solution is mixed thoroughly with 800 g of micronized silicic acid. The mixture is evaporated to dryness and then filled into hard gelatin capsules.

EXAMPLE 23

10,000 capsules with an active compound content of 25 mg are prepared as follows:

250 g of 2-[6-(4-chlorophenoxy)hexyl]oxirane-2-carboxylic acid ethyl ester are dissolved in 1,000 ml of methylene chloride. The solution is mixed thoroughly with 750 g of micronized silicic acid. The mixture is evaporated to dryness and then filled into hard gelatin capsules.

EXAMPLE 24

Tablets containing 25 mg of active compound are prepared as follows:

1 kg of sodium 2-[4-(3-trifluoromethylphenoxy)-butyl]-oxirane-2-carboxylate, 4.5 kg of xylit, 3.0 kg of calcium phosphate and 0.25 kg of polyvinylpyrrolidone (MG 25,000; MG = molecular weight) are moistened with approx. 0.5 liter of water and granulated through a sieve with a mesh width of 1.25 mm. The granules are dried and 0.9 kg of carboxymethylcellulose, 0.25 kg of talc and 0.1 kg of magnesium stearate are then added. The dry granules are compressed to give tablets weighing 250 mg, having a diameter of 8 mm and a hardness of 5 to 6 kg.

EXAMPLE 25

10,000 capsules with an active compound content of 20 mg are prepared as follows:

200 g of 2-[5-(4-chlorophenoxy)pentyl]oxirane-2-carboxylic acid ethyl ester are dissolved in 1,000 ml of methylene chloride. The solution is mixed thoroughly with 800 g of micronized silicic acid. The mixture is evaporated to dryness and then filled into hard gelatin capsules.

The following Examples describe the preparation of starting materials which are reacted analogously to the process of Genzer et al.

EXAMPLE A

2-[3-(5-Chloro-2-methoxyphenyl)propyloxy]ethyl chloride- 11.2 g of 2-[3-(5-chloro-2-methoxyphenyl)propyloxy]-ethanol and 20 ml thionyl chloride are stirred at 50° C. for 3 hours; the excess thionyl chloride is distilled off in vacuo. 11.3 g of 2[3-(5-chloro-2-methoxyphenyl)-propyloxy]ethyl chloride are obtained as a brown oil.

(b) 2-[3-(5-Chloro-2-methoxyphenyl)propyloxy]e-thanol- 10 ml of xylene are added to a solution of 1.6 g of sodium in 20 g of ethyleneglycol. A solution of 21.9 g of 2-(5-chloro-2-methoxyphenyl)propyl chloride in 10 ml of xylene are then successively added dropwise. The resulting mixture is boiled for one hour under reflux, allowed to cool, mixed with 100 ml of water and extracted three times with 100 ml of diethyl ether each time. The united organic phases are dried over sodium sulfate and concentrated. 11.2 g of 2-[3-(5-chloro-2-methoxyphenyl)propyloxy]ethanol are obtained as a brown oil.

(c) 3-(5-Chloro-2-methoxyphenyl)propyl chloride-
58.2 g of 3-(5-chloro-2-methoxyphenyl)propan-1-ol and 50 ml of thionyl chloride are stirred at 50° C. for 8 hours; the excess thionyl chloride is distilled off in vacuo and the residue is distilled under a high vacuo. 50.9 g of 3-(5-chloro-2-methoxyphenyl)propyl chloride of b.p. 87° to 95° C. under 0.005 mm Hg are obtained.

(d) 3-(5-Chloro-2-methoxyphenyl)propan-1-ol-
66.7 g of 3-(5-chloro-2-methoxyphenyl)propan-1-ol of b.p. 94° to 97° C. under 0.001 mm Hg are obtained from 96.6 g of 3-(5-chloro-2-methoxyphenyl)propionic acid and 14 g of lithium aluminum hydride in 900 ml of diethyl ether by the procedure described in Example Bd).

(e) 3-(5-Chloro-2-methoxyphenyl)propionic acid-
63.2 g of 3-(5-chloro-2-methoxyphenyl)propionic acid of m.p. 91° to 92° C. are obtained by saponifying 124 g of 5-chloro-2-methoxybenzylmalonic acid diethyl ester with potassium hydroxide and heating the resulting 5-chloro-2-methoxybenzylmalonic acid to 160° to 170° C. 5-Chloro-2-methoxybenzylmalonic acid diethyl ester is obtained from 100 g of 5-chloro-2-methoxybenzyl chloride, 120 ml of malonic acid diethyl ester and a solution of 12.07 g of sodium in 1.1 l of ethanol by the procedure described in Example B(e).

EXAMPLE B (a) 3-[3-(4-Fluorophenyl)propyloxy]propyl chloride-
10.0 g of 3-[3-(4-fluorophenyl)propyloxy]propyl chloride are obtained from 9.9 g of 3-[3-(4-fluorophenyl)propyloxy]propanol-1 and 20 ml thionyl chloride by the procedure described in Example A(a).

(b) 3-[3-(4-Fluorophenyl)propyloxy]propanol-1-
9.9 g of 3-[3-(4-fluorophenyl)propyloxy]propanol-1 (brown oil) are obtained from a solution of 1.6 g of sodium in 25 g of 1,3-propanediol, 20 ml of xylene and 17.2 g of 3-(4-fluorophenyl)propyl chloride by the procedure described in Example A(b).

(c) 3-(4-Fluorophenyl)propyl chloride-
30.2 g of 3-(4-fluorophenyl)propyl chloride (oil) are obtained from 35 g of 3-(4-fluorophenyl)propanol-1 and 30 ml of thionyl chloride by the procedure described in Example A(c).

(d) 3-(4-Fluorophenyl)propan-1-ol-
A solution of 43.6 g of 3-(4-fluorophenyl)propionic acid in 300 ml of tetrahydrofuran is added dropwise to a suspension of 19.7 g of lithium aluminum hydride in 300 ml of tetrahydrofuran at a reaction temperature of about 45° C., while stirring. When the addition has ended, the above temperature is maintained for a further 2.5 hours and 80 ml of water and 20 ml of 4 N sodium hydroxide solution are then successively added dropwise. The precipitate is filtered off and rinsed several times with diethyl ether and the combined solutions are dried over sodium sulfate and concentrated. 39.7 g of 3-(4-fluorophenyl)propan-1-ol remain as an almost colorless oil.

(e) 3-(4-Fluorophenyl)propionic acid-
91.6 g of malonic acid diethyl ester are added dropwise to a solution of 12.6 g of sodium in 300 ml of ethanol; the mixture is subsequently stirred for a further 15 minutes and 98.3 g of 4-fluorobenzyl bromide are then added dropwise. The mixture is subsequently boiled for a further 3 hours under reflux, most of the solvent is distilled off, the residue is taken up in ice-water (800 ml) and methylene chloride (600 ml) and the mixture is shaken thoroughly. The organic phase is collected and concentrated and the oil which remains (4-fluorobenzylmalonic acid diethyl ester) (137.6 g) is stirred with a solution of 133 g of potassium hydroxide in 780 ml of methanol for 12 hours. The mixture is substantially concentrated in vacuo, the residue is dissolved in water/diethyl ether, the solution is shaken thoroughly, the organic phase is separated off and the aqueous phase is acidified with 10 N sulfuric acid, while cooling with ice. The mixture is extracted with methylene chloride, the organic phase is concentrated and the oily residue is stirred with petroleum ether/ethyl acetate (3:1), whereupon 53.6 g of 4-fluorobenzylmalonic acid crystallize out (m.p. 134° to 136° C.).

The 4-fluorobenzylmalonic acid is heated to 170° to 175° C. for 1.5 hours. After cooling, the reaction product is stirred with a little diethyl ether. 41.6 of 3-(4-fluorophenyl)propionic acid of m.p. 85° to 88° C. [from ethyl acetate/petroleum ether (1:4)] thereby crystallize out.

EXAMPLE C (a) 3-(3-Trifluoromethylphenyl)propyl chloride-
10.3 g 3-(3-trifluoromethylphenyl)propyl chloride (oil) are obtained from 12 g of 3-(3-trifluoromethylphenyl)propanol-1 and 10 g of thionyl chloride by the procedure described in Example A(a).

(b) 3-(3-Trifluoromethylphenyl)propan-1-ol-
A solution of 57 g of oxirane in 120 ml of diethyl ether is added dropwise, at 0° to 10° C., to a Grignard solution prepared from 14.8 g of magnesium and 100 g of 3-(chloromethyl)benzotrifluoride in 450 ml of diethyl ether. The mixture is subsequently stirred at room temperature for 1 hour and 300 ml of 10% strength sulfuric acid are then added, while cooling with ice. The organic phase is collected and extracted twice more with diethyl ether and the combined organic phases are dried over magnesium sulfate and distilled. 76.7 g of 3-(3-trifluoromethylphenyl)propan-1-ol of b.p. 85° to 95° C. under 0.02 mm Hg are obtained.

Pharmacology

The substituted oxiranecarboxylic acids of formula I according to the invention lower the level of glucose and of ketones in the blood. Their chemical structure differs from that of beta-cytotropic substances (for example sulfonyl-ureas) which have an action on the pancreas, and their mode of action differs fundamentally from that of these substances in that they have an extra-pancreatic action. They are superior to commercial preparations (for example Buformin and Phenformin) having an extra-pancreatic action.

In the following Table the investigated compounds are characterized by a serial number, which is allocated as follows:

| Serial No. | Name of Compound |
|---|---|
| 1 | Buformin |
| 2 | Phenformin |
| 3 | 2-[4-(3-Chlorophenoxy)butyl]oxirane-2-carboxylic acid ethyl ester |
| 4 | 2-[4-(3-Trifluoromethylphenoxy)butyl]oxirane-2-carboxylic acid ethyl ester |
| 5 | 2-[6-(4-Chlorophenoxy)hexyl]oxirane-2-carboxylic acid ethyl ester |
| 6 | 2-[5-(4-Chlorophenoxy)pentyl]oxirane-2-carboxylic acid ethyl ester |
| 7 | 2-[4-(4-Methylphenoxy)butyl]oxirane-2-carboxylic acid ethyl ester |

Table I reflects investigations of the effect of representative compounds according to the invention on the blood glucose concentration of fasting, metabolically healthy rats which are observed for 6 hours after a single oral administration of from 0.01 to 0.6 mmol of substance/kg of body weight.

Column A states the dose of active compound (mg/kg) which effects (in 50% of the animals) a lowering of the blood glucose concentration by at least 25% with reference to a control group. Column B states the dose of active compound (mg/kg) which effects (in 50% of the animals) a lowering of the blood glucose concentration by at least 15% with reference to the control group. Column C provides data relating to acute toxicity ($LD_{50}$; mice, peroral administration).

TABLE I

| Serial No. | A $ED_{50}$ (25%) [mg/kg] rats p.o. | B $ED_{50}$ (15%) [mg/kg] rats p.o. | C $LD_{50}$ [mg/kg] mice p.o. |
|---|---|---|---|
| 1 | 194 | >100 | 475 |
| 2 | >343 | >150 | 410* |
| 3 | 24 | 3 | 390 |
| 4 | 13 | ~7 | 460 |
| 5 | 7 | <7 | 300 |
| 6 | 6 | 5 | 310 |
| 7 | 19 | 8 | |

Re Table I:
*Cited according to Blickens, D.A.; Riggi, S.J.: Toxicol. Appl. Pharmacol., 14 (1969)393-400
Column A = dose, which effects a lowering of the blood glucose concentration by 25% in 50% of the animals
Column B = dose, which effects a lowering of the blood glucose concentration by 15% in 50% of the animals
Column C = acute toxicity ($LD_{50}$ in mg/kg; mice, peroral administration).

The pharmacological properties were determined by the following methods:

1. Determination of glucose in the blood after a single oral administration-

Young male Sprague-Dawley rats (body weight: 150 to 200 g) are used. The animals are kept in Makrolon cages with up to 4 animals per cage (ambient temperature: 23° C., relative atmospheric humidity: 55%, fixed day/night rhythm [12/12 hours], standard diet: Altromin ®). The rats are deprived of the feed 18 hours before the first sample of blood is taken. Water is available ad libitum. Samples of blood are taken from the postorbital plexus by puncture immediately before and 3 and 6 hours after administration of the substance.

After deproteinization with perchloric acid, the glucose in the blood is determined by means of the enzymatic HK/G-6-PDH method of R. Richterich [Klinische Chemie, Theorie und Praxis, (Clinical Chemistry, Theory and Practice), 3rd edition, 1971, S. Karger Verlag, Zurich-Basle, page 275]. A control group (treated with pure solvent) is also investigated in each case for comparison.

2. Determination of the toxicity-

The toxicity investigations are carried out on female NMRI mice (body weight: 22 to 26 g). 18 hours before the treatment, the feed (Altromin ®) for the animals (5 animals per dose) is reduced to 50 g/50 animals and water is available ad libitum. Various doses of the substances (volume: 10 ml/kg) are administered orally by means of a stomach tube. The observation time is 7 days. The $LD_{50}$, that is to say the dose at which 50% of the animals die, is determined graphically from the dose/response curve.

The invention and its advantages are readily understood from the preceding description. Various changes may be made in the synthesis, the intermediates, the pharmacologically-active final products, the dosage forms, the medicament compositions, the mode of administration and treatment regimes without departing from the spirit and scope of the invention or sacrificing its material advantages. The hereinbefore described aspects of the subject invention are merely illustrative of preferred embodiments.

What is claimed is:

1. A substituted oxiranecarboxylic acid of the formula

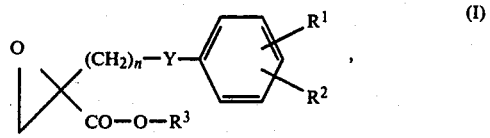

wherein
$R^1$ is —H, halo, lower alkyl, lower alkoxy, nitro or trifluoromethyl,
$R^2$ has one of the meanings of $R^1$,
$R^3$ is —H or lower alkyl,
Y is —O—$(CH_2)_m$—,
m is O or an integer from 1 to 4, inclusive, and
n is an integer from 2 to 8, inclusive, with the proviso that m+n is an integer from 2 to 8, inclusive,
or a salt of each carboxylic acid.

2. A substituted oxiranecarboxylic acid according to claim 1,
wherein
$R^1$ and $R^2$ are in the meta-position or para-position,
$R^1$ is —H, chloro, methyl, methoxy or trifluoromethyl,
$R^2$ is —H or chloro,
$R^3$ is —H or lower alkyl,
Y is —O—$(CH_2)_m$,
m is O or 1, and
n is an integer from 3 to 7, inclusive,
with the proviso that m—n is an integer from 3 to 7, inclusive,
or a salt of each carboxylic acid with a base.

3. A substituted oxiranecarboxylic acid according to claim 1,
wherein
$R^1$ is in the meta-position or para-position, $R^1$ is —H, chloro or trifluoromethyl,
$R^2$ is —H,
$R^3$ is —H, methyl or ethyl,
Y is —O— and
n is an integer from 4 to 6, inclusive, or a pharmacologically-acceptable salt of each carboxylic acid with an inorganic or organic base.

4. A compound according to claim 3, wherein $R^1$ is —H.

5. A compound according to claim 3, wherein $R^1$ is chloro.

6. A compound according to claim 3, wherein $R^1$ is trifluoromethyl.

7. A medicament composition comprising physiologically-acceptable excipient in combination with from 2 to 200 milligrams per unit dose of a pharmacologically-acceptable compound of one of claims 1 to 6 and 16 to 19.

8. A medicament composition for the prophylaxis or treatment of a glucose or fat metabolism disorder which comprises physiologically-acceptable excipient in combination with an effective amount of a pharmacologically-acceptable compound of one of claims 1 to 6 and 16 to 19.

9. A method for the prophylaxis or treatment of a glucose or fat metabolism disorder which comprises administering an effective amount of a pharmacologically-acceptable compound according to one of claims 1 to 6 and 16 to 19 to a mammal subject to or afflicted with such disorder.

10. The compound according to claim 1 which is 2-[4-(3-chlorophenoxy)butyl]oxirane-2-carboxylic acid ethyl ester.

11. The compound according to claim 1 which is 2-[5-(4-chlorophenoxy)pentyl]oxirane-2-carboxylic acid ethyl ester.

12. A phenalkoxyalkyl-substituted oxiranecarboxylic acid according to claim 1 or a salt thereof.

13. A phenoxyalkyl-substituted oxiranecarboxylic acid according to claim 1 or a salt thereof.

* * * * *

UNITED STATES PATENT AND TRADEMARK OFFICE
CERTIFICATE OF CORRECTION

PATENT NO. : 4,337,267
DATED : June 29, 1982
INVENTOR(S) : Klaus EISTETTER and Erich RAPP         Page 1 of 2

It is certified that error appears in the above-identified patent and that said Letters Patent are hereby corrected as shown below:

Title page, line 1 of the ABSTRACT, "Phenalkoxyalky-" should read --Phenalkoxyalkyl- --. Column 4, line 33, "2[7" should read --2-[7--; line 35, "2[7" should read --2-[7--; line 64, "ethyl ester, ... ethyl ester," should read --ethyl ester,--. Column 5, line 35, "chlorphenyl" should read --chlorophenyl--; line 39, "2[6" should read --2-[6--; line 46, after "ester," start a new line with "the corresponding"; that text and the rest of the sentence should not be indented. Column 8, line 67, in the formula, "CO-C-$R^3$" should read --CO-O-$R^3$--. Column 9, line 47, "benezene" should read --benzene--. Column 10, line 11, "oxiranecarboyxlic" should read --oxiranecarboxylic--. Column 11, line 62, "ester -" should read --ester — --. Column 12, lines 13, 25, 45, 54 and 62, "ester -" should read --ester — --; line 52, "Example 1a)," should read --Example 1a).--; line 65, "44-" should read --4-(4- --. Column 13, lines 2, 22, 32, 42 and 50, "ester -" should read --ester — --; line 26, "1:1]" should read --1:1)]--; line 36, "1:1]" should read --1:1)]--; line 57, "bromide -" should read --bromide — --. Column 14, lines 6, 14, 21 and 22, 30, 41, 49, 56 and 67, "ester -" should read --ester — --; line 45, "chloride]" should read --chloride)]--. Column 15, lines 7, 14, 25, 33, 46, 58 and 65, "ester -" should read --ester — --; line 18, "1.2" should read --1.2 1--; line 40, "6-(4" should read --6-(4-Chlorophenoxy)hexylmalonic acid ethyl ester —

74 g of 6-(4--. Column 16, lines 4 and 5, 12, 24, 32 and 33, 40, 52, 60 and 68, "ester -" should read --ester — --; line 10, "Example b 1c)" should read --Example 1c)--; line 27, "9:1]" should read --9:1)]--; line 38, "describe" should read --described--. Column 17, lines 7, 21, 29, 38 and 44, "ester -" should read --ester — --. Column 18, line 62, "ester -" should read --ester — --; line 65, "9:1" should read --9:1)]--. Column 19, lines 2, 10, 17, 31, 39, 47 and 53, "ester -" should read --ester — --; line 13, ")-ethylmalonic" should read --)ethylmalonic--; line 47, "19.5 g" should start a new paragraph. Column 20, line 16, "chloride" should read --chloride.--; line 45, "butyl]-oxirane" should read --butyl]oxirane--. Column 21, lines 2, 23, 50 and 61, "chloride -" should read --chloride — --; line 4, "y]-ethanol" should

UNITED STATES PATENT AND TRADEMARK OFFICE
CERTIFICATE OF CORRECTION

PATENT NO. : 4,337,267

DATED : June 29, 1982

INVENTOR(S) : Klaus EISTETTER and Erich RAPP           Page 2 of 2

It is certified that error appears in the above-identified patent and that said Letters Patent are hereby corrected as shown below:

read --y]ethanol--; line 8, "2[3" should read --2-[3--; line 11, "thanol -" should read --thanol — --; lines 30 and 66, "ol -" should read --ol — --; line 36, "Bd)." should read --B(d).--; line 37, "acid -" should read --acid — --; line 55, "-1-" should read -- -1 — --. Column 22, line 12, "acid -" should read --acid — --; line 43, "chloride -" should read --chloride — --; line 48, "ol -" should read --ol — --. Column 23, line 48, "14" should read --*14*--; line 58, "administration -" should read --administration — --. Column 24, line 9, "toxicity -" should read --toxicity — --; line 62, "m-n" should read --m+n--. Column 25, lines 17 and 18, "16 to 19" should read --10 to 13--. Column 26, lines 2 and 3, "16 to 19" should read --10 to 13--; line 8, "16 to 19" should read --10 to 13--.

Signed and Sealed this

Twenty-fourth Day of May 1983

[SEAL]

Attest:

DONALD J. QUIGG

*Attesting Officer*    *Acting Commissioner of Patents and Trademarks*